(12) United States Patent
Syed

(10) Patent No.: US 10,173,031 B2
(45) Date of Patent: Jan. 8, 2019

(54) INTERCHANGEABLE FLUSH/SELECTIVE CATHETER

(71) Applicant: Mubin I. Syed, Springfield, OH (US)

(72) Inventor: Mubin I. Syed, Springfield, OH (US)

(*) Notice: Subject to any disclaimer, the term of this patent is extended or adjusted under 35 U.S.C. 154(b) by 0 days.

(21) Appl. No.: 15/225,667

(22) Filed: Aug. 1, 2016

(65) Prior Publication Data

US 2017/0361062 A1 Dec. 21, 2017

Related U.S. Application Data

(60) Provisional application No. 62/352,492, filed on Jun. 20, 2016.

(51) Int. Cl.
*A61M 25/00* (2006.01)

(52) U.S. Cl.
CPC ...... *A61M 25/0026* (2013.01); *A61M 25/007* (2013.01); *A61M 2025/0019* (2013.01); *A61M 2025/0039* (2013.01); *A61M 2202/0085* (2013.01)

(58) Field of Classification Search
CPC ............ A61M 25/0026; A61M 25/007; A61M 2025/0019; A61M 2025/0039; A61M 2202/0085
See application file for complete search history.

(56) References Cited

U.S. PATENT DOCUMENTS

| 4,243,040 | A | | 1/1981 | Beecher |
| 5,098,707 | A | | 3/1992 | Baldwin et al. |
| 5,293,772 | A | | 9/1994 | Carr, Jr. |
| 5,344,426 | A | | 9/1994 | Lau et al. |
| 5,419,777 | A | | 5/1995 | Hofling |
| 5,571,135 | A | | 11/1996 | Fraser et al. |
| 5,651,366 | A | | 7/1997 | Liang et al. |
| 5,662,703 | A | | 9/1997 | Yurek et al. |
| 5,669,924 | A | | 9/1997 | Shaknovich |
| 5,690,644 | A | | 11/1997 | Yurek et al. |
| 5,718,702 | A | | 2/1998 | Edwards |
| 5,720,735 | A | | 2/1998 | Dorros |
| 5,807,330 | A | * | 9/1998 | Teitelbaum ............. A61F 2/958 604/509 |

(Continued)

FOREIGN PATENT DOCUMENTS

| CN | 108472124 A | 8/2018 |
| CN | 108472472 A | 8/2018 |

(Continued)

OTHER PUBLICATIONS

International Search Report / Written Opinion issued in Int'l Application No. PCT/US2013/071271 dated Feb. 10, 2014, 7 pages.

(Continued)

*Primary Examiner* — Lauren P Farrar
(74) *Attorney, Agent, or Firm* — Jennifer Hayes; Nixon Peabody LLP

(57) ABSTRACT

A combination flush catheter and selective catheter as one convertible catheter and methods of using the same. The selective catheter may be a reverse curve or guide catheter. The additional steps of removal of the flush catheter and re-insertion of the selective catheter may be eliminated, reducing the possibility of errors and making the procedure smoother and shorter.

9 Claims, 7 Drawing Sheets

(56) References Cited

U.S. PATENT DOCUMENTS

| | | | |
|---|---|---|---|
| 5,957,901 A * | 9/1999 | Mottola | A61M 25/007 604/264 |
| 6,027,462 A | 2/2000 | Greene et al. | |
| 6,059,813 A | 5/2000 | Vrba et al. | |
| 6,070,589 A | 6/2000 | Keith et al. | |
| 6,152,141 A | 11/2000 | Stevens et al. | |
| 6,238,410 B1 | 5/2001 | Vrba et al. | |
| 6,245,017 B1 | 6/2001 | Hashimoto | |
| 6,450,964 B1 | 9/2002 | Webler | |
| 6,544,278 B1 | 4/2003 | Vrba et al. | |
| 6,663,613 B1 | 12/2003 | Lewis et al. | |
| 6,780,174 B2 | 8/2004 | Mauch | |
| 6,808,520 B1 * | 10/2004 | Fourkas | A61B 17/3462 604/164.09 |
| 6,837,881 B1 | 1/2005 | Barbut | |
| 6,929,633 B2 | 8/2005 | Evans et al. | |
| 6,942,682 B2 | 9/2005 | Vrba et al. | |
| 7,235,083 B1 | 6/2007 | Perez et al. | |
| 7,393,358 B2 | 7/2008 | Malewicz | |
| 7,758,624 B2 | 7/2010 | Dorn et al. | |
| 7,763,010 B2 | 7/2010 | Evans et al. | |
| 7,766,961 B2 | 8/2010 | Patel et al. | |
| 7,842,026 B2 | 11/2010 | Cahill et al. | |
| 7,955,370 B2 | 6/2011 | Gunderson | |
| 8,092,509 B2 | 1/2012 | Dorn et al. | |
| 8,202,309 B2 | 6/2012 | Styrc | |
| 8,241,241 B2 | 8/2012 | Evans et al. | |
| 8,343,181 B2 | 1/2013 | Duffy et al. | |
| 8,535,290 B2 | 9/2013 | Evans et al. | |
| 8,721,714 B2 | 5/2014 | Kelley | |
| 8,727,988 B2 | 5/2014 | Flaherty et al. | |
| 8,740,971 B2 | 6/2014 | Iannelli | |
| 8,986,241 B2 | 3/2015 | Evans et al. | |
| 8,998,894 B2 | 4/2015 | Mauch et al. | |
| 9,314,499 B2 | 4/2016 | Wang et al. | |
| 9,636,244 B2 | 5/2017 | Syed | |
| 9,980,838 B2 | 5/2018 | Syed | |
| 2001/0003985 A1 | 6/2001 | Lafontaine et al. | |
| 2001/0049534 A1 | 12/2001 | Lachat | |
| 2002/0077691 A1 | 6/2002 | Nachtigall | |
| 2002/0123698 A1 | 9/2002 | Garibotto et al. | |
| 2002/0156518 A1 | 10/2002 | Tehrani | |
| 2002/0165535 A1 | 11/2002 | Lesh | |
| 2003/0088187 A1 | 5/2003 | Saadat et al. | |
| 2003/0216721 A1 | 11/2003 | Diederich | |
| 2003/0229282 A1 | 12/2003 | Burdette | |
| 2004/0073190 A1 | 4/2004 | Deem et al. | |
| 2004/0138734 A1 | 7/2004 | Chobotov et al. | |
| 2004/0147837 A1 | 7/2004 | Macaulay et al. | |
| 2005/0043779 A1 | 2/2005 | Wilson | |
| 2005/0101968 A1 | 5/2005 | Dadourian | |
| 2005/0113862 A1 | 5/2005 | Besselink et al. | |
| 2005/0222488 A1 | 10/2005 | Chang et al. | |
| 2006/0025752 A1 * | 2/2006 | Broaddus | A61M 25/00 604/537 |
| 2006/0025844 A1 | 2/2006 | Majercak et al. | |
| 2006/0030923 A1 | 2/2006 | Gunderson | |
| 2006/0155363 A1 | 7/2006 | Laduca et al. | |
| 2006/0200221 A1 | 9/2006 | Malewicz | |
| 2006/0257389 A1 | 11/2006 | Binford | |
| 2006/0259063 A1 | 11/2006 | Bates et al. | |
| 2006/0270900 A1 | 11/2006 | Chin et al. | |
| 2007/0016019 A1 | 1/2007 | Salgo | |
| 2007/0016062 A1 | 1/2007 | Park | |
| 2007/0038061 A1 | 2/2007 | Huennekens et al. | |
| 2007/0038293 A1 | 2/2007 | St. Goar et al. | |
| 2007/0049867 A1 | 3/2007 | Shindelman | |
| 2007/0083215 A1 | 4/2007 | Hamer et al. | |
| 2007/0118151 A1 | 5/2007 | Davidson et al. | |
| 2007/0129719 A1 | 6/2007 | Kendale et al. | |
| 2008/0039746 A1 | 2/2008 | Hissong et al. | |
| 2008/0114239 A1 | 5/2008 | Randall et al. | |
| 2008/0194993 A1 | 8/2008 | McLaren et al. | |
| 2008/0208309 A1 | 8/2008 | Saeed | |
| 2008/0281398 A1 | 11/2008 | Koss | |
| 2009/0005679 A1 | 1/2009 | Dala-Krishna | |
| 2009/0036780 A1 | 2/2009 | Abraham | |
| 2009/0132019 A1 | 5/2009 | Duffy et al. | |
| 2009/0171293 A1 | 7/2009 | Yang et al. | |
| 2009/0177035 A1 | 7/2009 | Chin | |
| 2009/0240253 A1 | 9/2009 | Murray | |
| 2009/0254116 A1 | 10/2009 | Rosenschein et al. | |
| 2009/0270975 A1 | 10/2009 | Giofford, III et al. | |
| 2009/0319017 A1 | 12/2009 | Berez et al. | |
| 2010/0016943 A1 | 1/2010 | Chobotov | |
| 2010/0024818 A1 | 2/2010 | Stenzler et al. | |
| 2010/0030165 A1 | 2/2010 | Takagi et al. | |
| 2010/0030256 A1 | 2/2010 | Dubrul et al. | |
| 2010/0069852 A1 | 3/2010 | Kelley | |
| 2010/0168583 A1 | 7/2010 | Dausch et al. | |
| 2010/0185161 A1 | 7/2010 | Pellegrino et al. | |
| 2010/0185231 A1 | 7/2010 | Lashinski | |
| 2010/0204708 A1 | 8/2010 | Sharma | |
| 2010/0268067 A1 | 10/2010 | Razzaque et al. | |
| 2010/0272740 A1 | 10/2010 | Vertegel et al. | |
| 2011/0009943 A1 | 1/2011 | Paul et al. | |
| 2011/0034987 A1 | 2/2011 | Kennedy | |
| 2011/0071394 A1 | 3/2011 | Fedinec | |
| 2011/0082533 A1 | 4/2011 | Vardi et al. | |
| 2011/0224773 A1 | 9/2011 | Gifford et al. | |
| 2011/0230830 A1 | 9/2011 | Gifford, III et al. | |
| 2011/0270375 A1 | 11/2011 | Hartley et al. | |
| 2012/0016343 A1 | 1/2012 | Gill | |
| 2012/0020942 A1 | 1/2012 | Hall et al. | |
| 2012/0022636 A1 | 1/2012 | Chobotov | |
| 2012/0029478 A1 | 2/2012 | Kurosawa | |
| 2012/0034205 A1 | 2/2012 | Alkon | |
| 2012/0035590 A1 | 2/2012 | Whiting et al. | |
| 2012/0169712 A1 | 7/2012 | Hill et al. | |
| 2012/0209375 A1 | 8/2012 | Madrid et al. | |
| 2012/0289945 A1 | 11/2012 | Segermark | |
| 2013/0053792 A1 | 2/2013 | Fischell et al. | |
| 2013/0131777 A1 | 5/2013 | Hartley et al. | |
| 2013/0296773 A1 | 11/2013 | Feng et al. | |
| 2013/0331819 A1 | 12/2013 | Rosenman et al. | |
| 2013/0331921 A1 | 12/2013 | Roubin | |
| 2014/0031925 A1 | 1/2014 | Garrison et al. | |
| 2014/0142427 A1 | 5/2014 | Petroff | |
| 2014/0214002 A1 | 7/2014 | Lieber et al. | |
| 2014/0228808 A1 | 8/2014 | Webster et al. | |
| 2015/0018942 A1 | 1/2015 | Hung et al. | |
| 2015/0174377 A1 | 6/2015 | Syed | |
| 2015/0190576 A1 | 7/2015 | Lee et al. | |
| 2015/0201900 A1 | 7/2015 | Syed | |
| 2015/0245933 A1 | 9/2015 | Syed | |
| 2015/0352331 A1 | 12/2015 | Helm, Jr. | |
| 2015/0366536 A1 | 12/2015 | Courtney et al. | |
| 2015/0374261 A1 | 12/2015 | Grunwald | |
| 2016/0008058 A1 * | 1/2016 | Hu | A61M 25/0147 606/21 |
| 2016/0038724 A1 | 2/2016 | Madsen et al. | |
| 2016/0120509 A1 | 5/2016 | Syed | |
| 2016/0120673 A1 | 5/2016 | Siegel et al. | |
| 2016/0296355 A1 | 10/2016 | Syed | |
| 2016/0338835 A1 | 11/2016 | Van Bladel et al. | |
| 2017/0119562 A1 | 5/2017 | Syed | |
| 2017/0119563 A1 | 5/2017 | Syed | |
| 2017/0135833 A1 | 5/2017 | Syed | |
| 2017/0181876 A1 | 6/2017 | Syed | |
| 2017/0304095 A1 | 10/2017 | Syed | |
| 2018/0042743 A1 | 2/2018 | Syed | |
| 2018/0059124 A1 | 3/2018 | Syed | |
| 2018/0250147 A1 | 9/2018 | Syed | |

FOREIGN PATENT DOCUMENTS

| | | |
|---|---|---|
| EP | 3280355 A1 | 2/2018 |
| EP | 3367969 A1 | 9/2018 |
| EP | 3368123 A1 | 9/2018 |
| WO | 1996036269 | 11/1996 |
| WO | 2011/011539 A1 | 1/2011 |
| WO | WO2011/106502 | 9/2011 |
| WO | 2010/129193 A1 | 11/2011 |
| WO | 2011/137336 A1 | 11/2011 |

(56) References Cited

FOREIGN PATENT DOCUMENTS

| WO | 2012030101 | 8/2012 |
| --- | --- | --- |
| WO | 2014081947 | 5/2014 |
| WO | 2014197839 | 12/2014 |
| WO | 2016164215 | 10/2016 |
| WO | 2017/074492 A1 | 5/2017 |
| WO | 2017/074536 A1 | 5/2017 |
| WO | 2017/127127 A1 | 7/2017 |
| WO | 2017222571 A1 | 12/2017 |
| WO | 2017222612 A1 | 12/2017 |

OTHER PUBLICATIONS

International Preliminary Report on Patentability issued in International Application No. PCT/US2013/071271 dated May 26, 2015, 6 pages.
Office Action issued in U.S. Appl. No. 13/750,920 dated Apr. 8, 2015.
Response to Office Action in U.S. Appl. No. 13/750,920 dated Aug. 10, 2015.
Supplemental Response to Office Action in U.S. Appl. No. 13/750,920 dated Nov. 2, 2015.
Office Action in U.S. Appl. No. 13/750,920 dated Nov. 5, 2015.
Response to Office Action in U.S. Appl. No. 13/750,920 dated Feb. 11, 2016.
International Search Report / Written Opinion issued in Int'l Application No. PCT/US2016/024794 dated Jul. 1, 2016, 10 pages.
International Search Report and Written Opinion issued for International Application No. PCT/US2016/047165 dated Jan. 5, 2017, 13 pages.
International Search Report and Written Opinion issued for International Application No. PCT/US2017/021188 dated May 10, 2017, 11 pages.
Stroke Treatments, American Heart Association, Retrieved from: Http://www.strokeassociation.org/STROKEORG/AboutStroke/Treatment/Stroke-Treatments_UCM_310892_Article_jsp#V9Hrg2WfV_1.
Beckman et al., Venous Thromboembolism: A Public Health Concern, Am J Prev Med., 2010, vol. 38(4), pp. S495-501.
Meunier et al., Individual Lytic Efficacy of Recombinant Tissue Plasminogen Activator in an in-vitro Human Clot Model: Rate of Nonresponse Acad Emerg Med., 2013, vol. 20(5), pp. 449-455.
Tripathi et al., Use of Tissue Plasminogen Activator for Rapoid Dissolution of Fibrin and Blood Clots in the Eye After Surgery for Claucomoa and Cataract in Humans, Drug Development Research, 1992, vol. 27(2), pp. 147-159.
International Search Report and Written Opinion for International Application No. PCT/US2016/024795 dated Aug. 30, 2016, 14 pages.
International Preliminary Report on Patentability issued in International Application No. PCT/US2016/024795 dated May 1, 2018, 10 pages.
International Preliminary Report on Patentability issued in International Application No. PCT/US2016/047165 dated May 1, 2018, 5 pages.
International Search Report and Written Opinion issued for PCT/US2018/012834 dated Mar. 15, 2018, 13 pages.
Godwin, J., The Circulatory and Respiratory Systems, Z0250 Lab III, 2002, retrieved from: https://projects.ncsu.edu/cals/course/zo250/lab-3.html.
Schwartz et al., Intracardiac Echocardiography in Humans using a Small-Sized (6F), Low Frequency (12.5 MHz) Ultrasound Catheter Methods, Imaging Planes and Clinical Experience, Journal of the American College of Cardiology, 1993, vol. 21(1), pp. 189-198.

\* cited by examiner

Enhanced multisidehole flush catheter mode

INTERCHANGEABLE FLUSH/SELECTIVE CATHETER

CROSS-REFERENCE TO RELATED APPLICATIONS

The present patent application claims priority to provisional application No. 62/352,492, entitled "Interchangeable Flush/Selective Catheter", filed Jun. 20, 2016, the entirety of which is herein incorporated by reference.

BACKGROUND

1. Field

The invention relates to improved methods for providing easy visibility and access for aortic catheters to identify the branching locations of interest and shortening the time taken for procedures.

2. Related Art

Today's catheters are used for minimally invasive life saving procedures especially procedures in the vessels branching off from the main arteries and or veins. These catheters are inserted percutaneously through the femoral artery or vain and guided through the main vessel under visual guidance typically using x-ray fluorescence. In order for the vessels to be visible by x-ray imaging and to identify the location of branching, etc., it is necessary to bathe the walls of the vessels, both veins and arteries to be flushed with a solution that contains the radiopaque compound. This is done by inserting a first catheter—a flush catheter having holes in the side wall that is used to spray the radiopaque compound on to the arterial or venous walls thereby making them visible in the x-ray fluoroscope. This action also helps to identify the openings and origins of vessels branching off or originating from the main vessel. Once the branch or vessel of importance is identified, the flush catheter is removed and a selective catheter such as a guide catheter/or reverse curve catheter is inserted percutaneously to access the identified opening of the vessel where the procedure is needed or the branch vessel. This requires an accurate judgment of the location of the opening from the main vessel to the vessel where the procedure is to be performed. This dual operation introduces complexity of an additional catheter introduction and also could result in problems of guiding the guide/or reverse curve catheter into the location of the procedure as the radiopaque contrast agent would have dissipated by the time the second catheter is introduced and guided to the location.

SUMMARY

The following summary of the invention is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

Embodiments of the invention relate to the capability to introduce a single selective catheter that can initially work as a flush catheter but can be converted to a guide/or reverse curve catheter once the process vessel is identified. This reduces the complexity of the procedure, reduces the time required for the procedure and reduces the errors in selection of the appropriate vessel that requires corrective procedure performed.

In accordance with one aspect of the invention, the use of a convertible catheter is disclosed that can act as a flush catheter and then convert to a selective catheter such as a reverse curve/guide catheter.

In accordance with one aspect of the invention, the structure of the flush/selective catheter is disclosed.

In accordance with one aspect of the invention, the ease of use of the disclosed catheter to identify the branches of interest and using the same as the converted selective catheter to access the site of the procedure.

In accordance with one aspect of the invention, the capability of the interchangeable flush/selective catheter to reduce errors and mistakes and reduce the time taken for the procedure.

BRIEF DESCRIPTION OF THE DRAWINGS

The accompanying drawings, which are incorporated into and constitute a part of this specification, illustrate one or more examples of embodiments and, together with the description of example embodiments, serve to explain the principles and implementations of the embodiments.

DETAILED DESCRIPTION

Embodiments of the invention combine a flush catheter and a selective catheter, such as the reverse curve or guide catheter, as one convertible catheter. The additional steps of removal of the flush catheter and re-insertion of the selective catheter, such as reverse curve or guide catheter, is eliminated, reducing the possibility of errors and making the procedure smoother and shorter.

Figure 1:
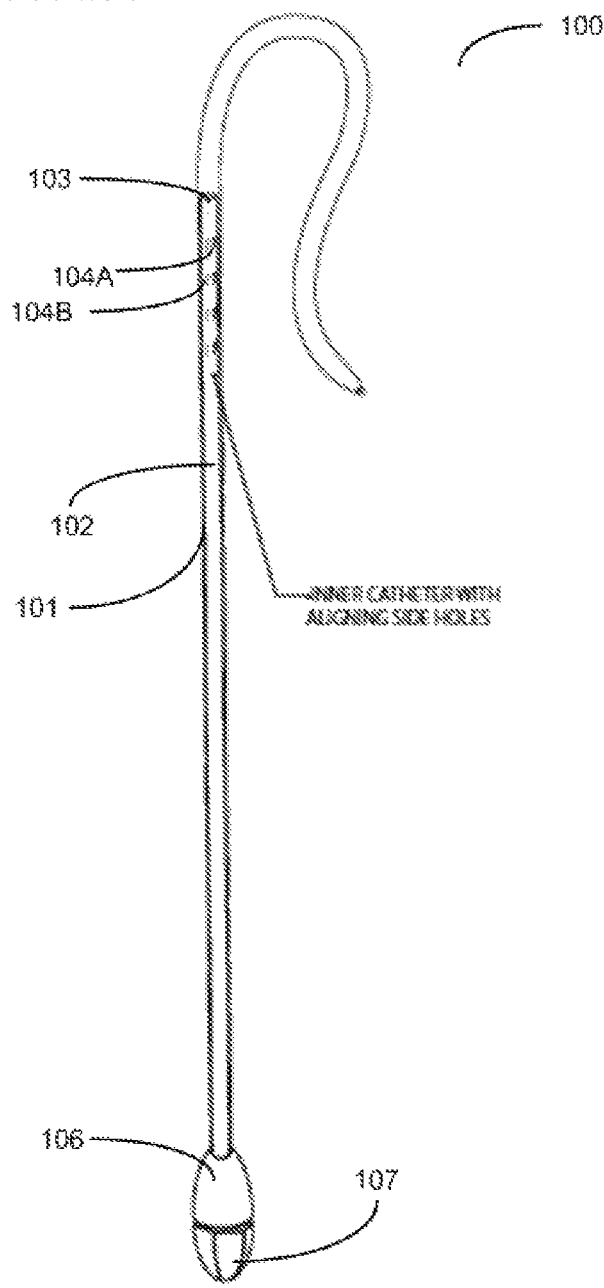
FIG. 1 is an exemplary diagrammatic representation of an interchangeable flush/selective catheter with the flush catheter holes in the closed condition in accordance with one embodiment of the invention.
Figure 1A:
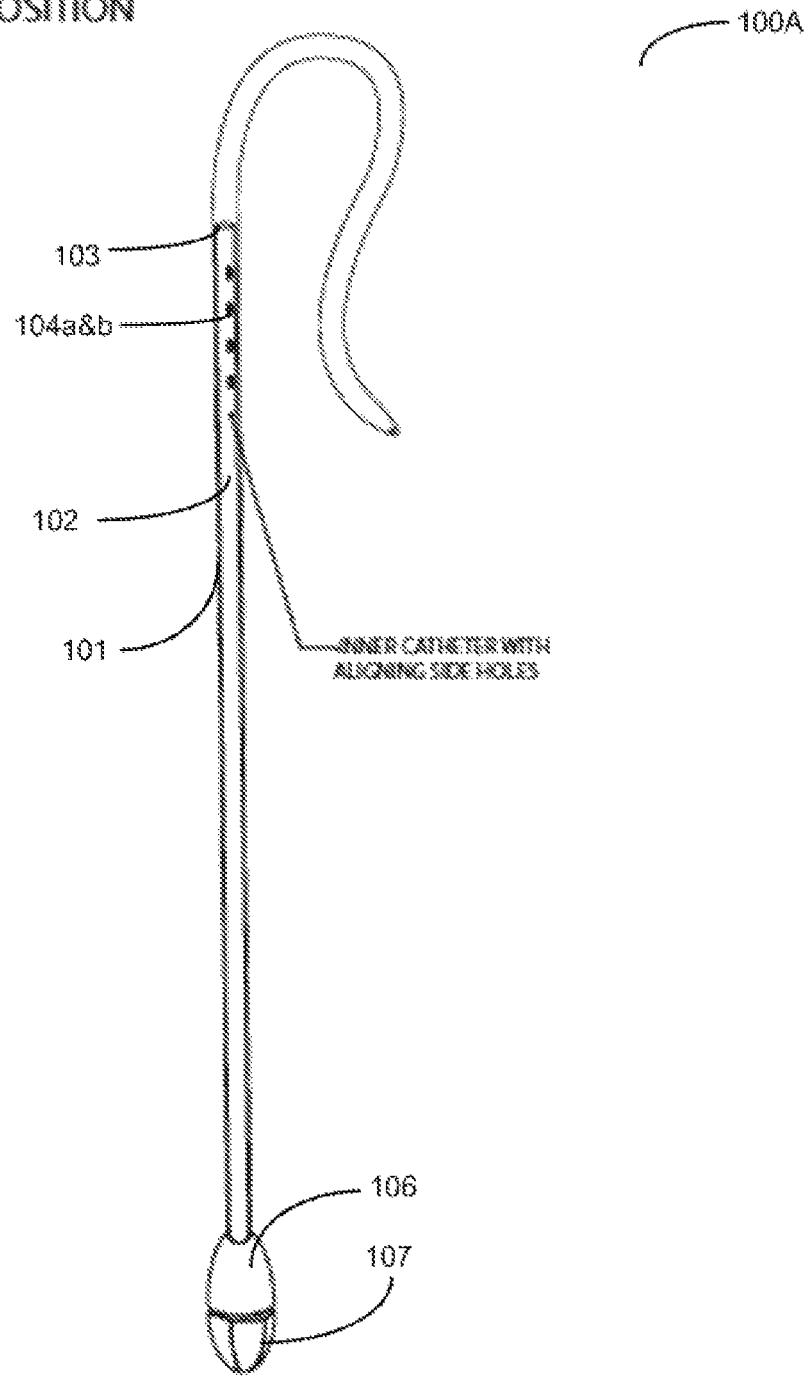
FIG. 1A is a diagrammatic representation of the catheter of FIG. 1 with the flush holes in the open flushing condition in accordance with one embodiment of the invention.

FIG. 1 is a diagrammatic representation of a first embodiment of the interchangeable flush/selective catheter 100 in the closed position as per a first embodiment of the invention with the flush catheter holes 104A on the outer catheter 101 misaligned with the holes 104B in the inner catheter 102 so as to place the flush/selective catheter 100 in the closed condition, that is the catheter is in an end hole angiographic catheter mode through the open end 103 of the inner catheter 102. FIG. 1A is a diagrammatic representation 100A of the flush/selective catheter 100 of FIG. 1 with the flush holes 104A and 104B in the aligned open flushing condition that is the flush/selective catheter 100 is in a multi-side-hole flush catheter mode. The change from a flush catheter mode to the end hole mode is done by twisting the inner catheter 102 with reference to the outer catheter 101. It is done by using the connector 106 connected to the outer catheter 101 and the twist connector 107 connected to the inner catheter 102. By twisting the twist connector 107 the flush/selective catheter can be made into an end-hole configuration or a flush catheter configuration.

Figure 1B:
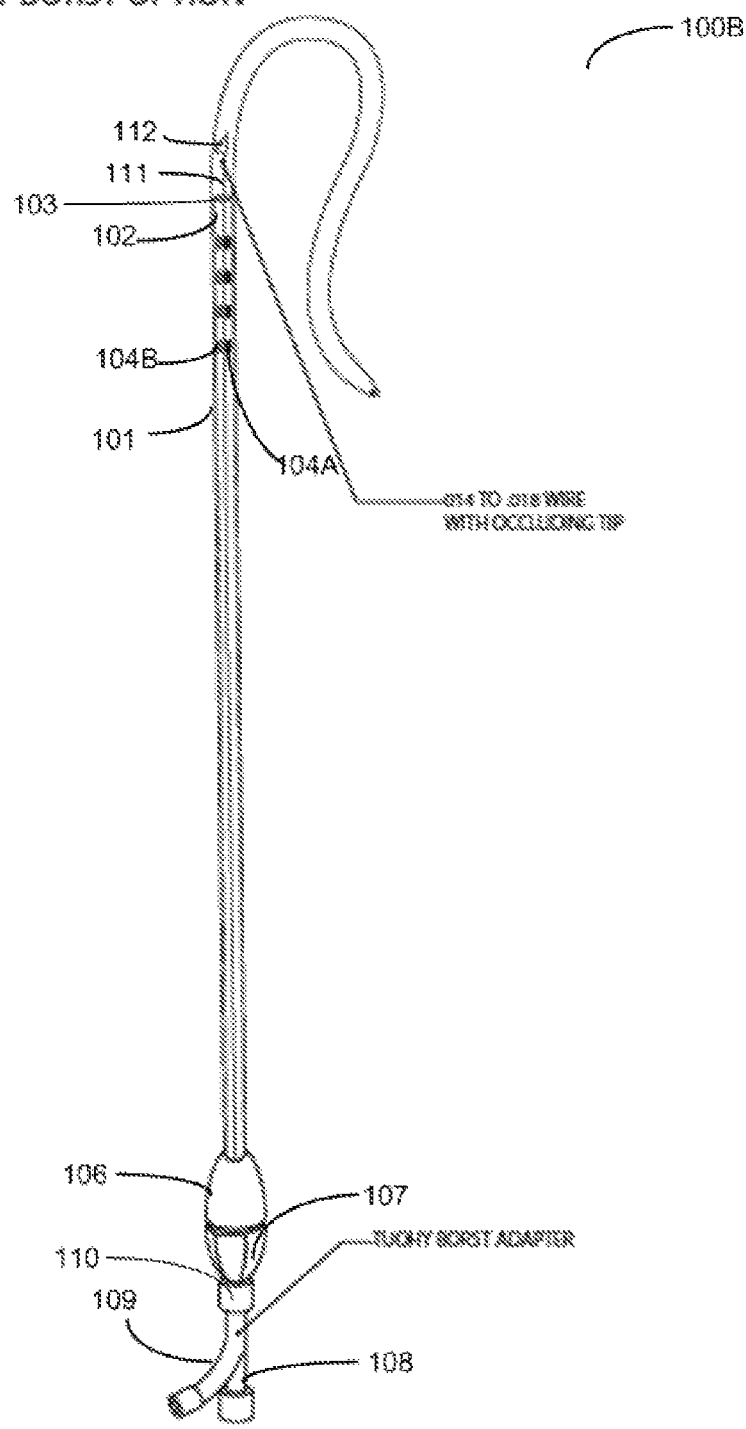
FIG. 1B is a diagrammatic representation of the catheter in FIG. 1 with a Tuohy Bost adapter attached to the base catheter and showing the use of an occluding mechanism for the catheter in accordance with one embodiment of the invention.

FIG. 1B shows the flush/selective catheter 100 implementation 100B with external connections through a Tuchy-Borst adaptor 110 having two connections 108 and 109 for connection to the inner and outer catheters 102 and 101 respectively. Use of the Tuchy-Borst adapter helps to provide reliable connection to the two catheters 102 and 101. Further the implementation includes an occluding tip 112 of occluding tip wire 111 which is used to close the open tip 103 of the inner catheter 102 when flush/selective catheter 100B is used as a flush catheter. The occluding tip wire may be removed when the catheter needs to serve as a selective catheter. The side-holes of the two coaxial catheters are misaligned during this time for conversion to selective catheter.

Figure 2:
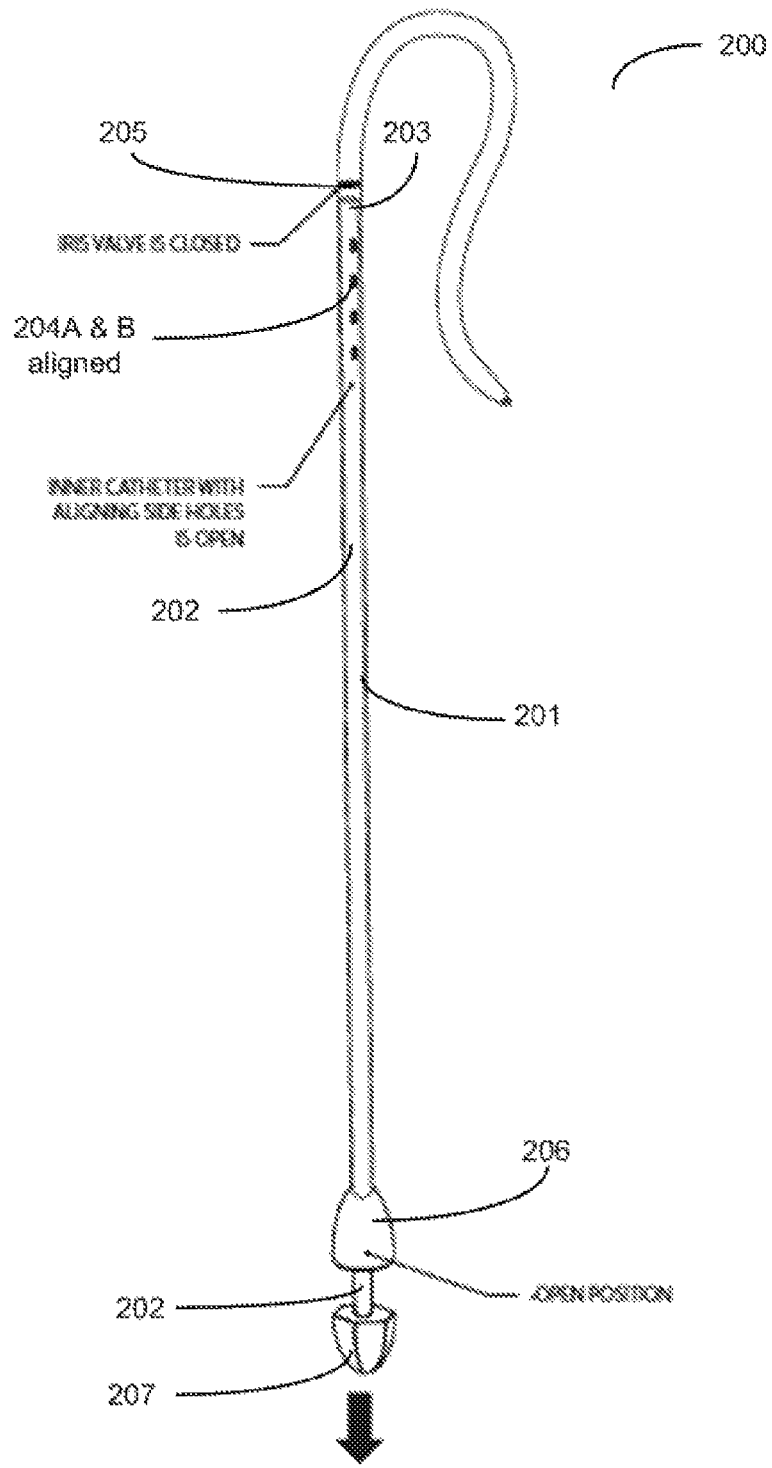
FIG. 2 is an exemplary diagrammatic representation of an interchangeable flush/selective catheter with the flush holes in open position in accordance with one embodiment of the invention.
Figure 2A:
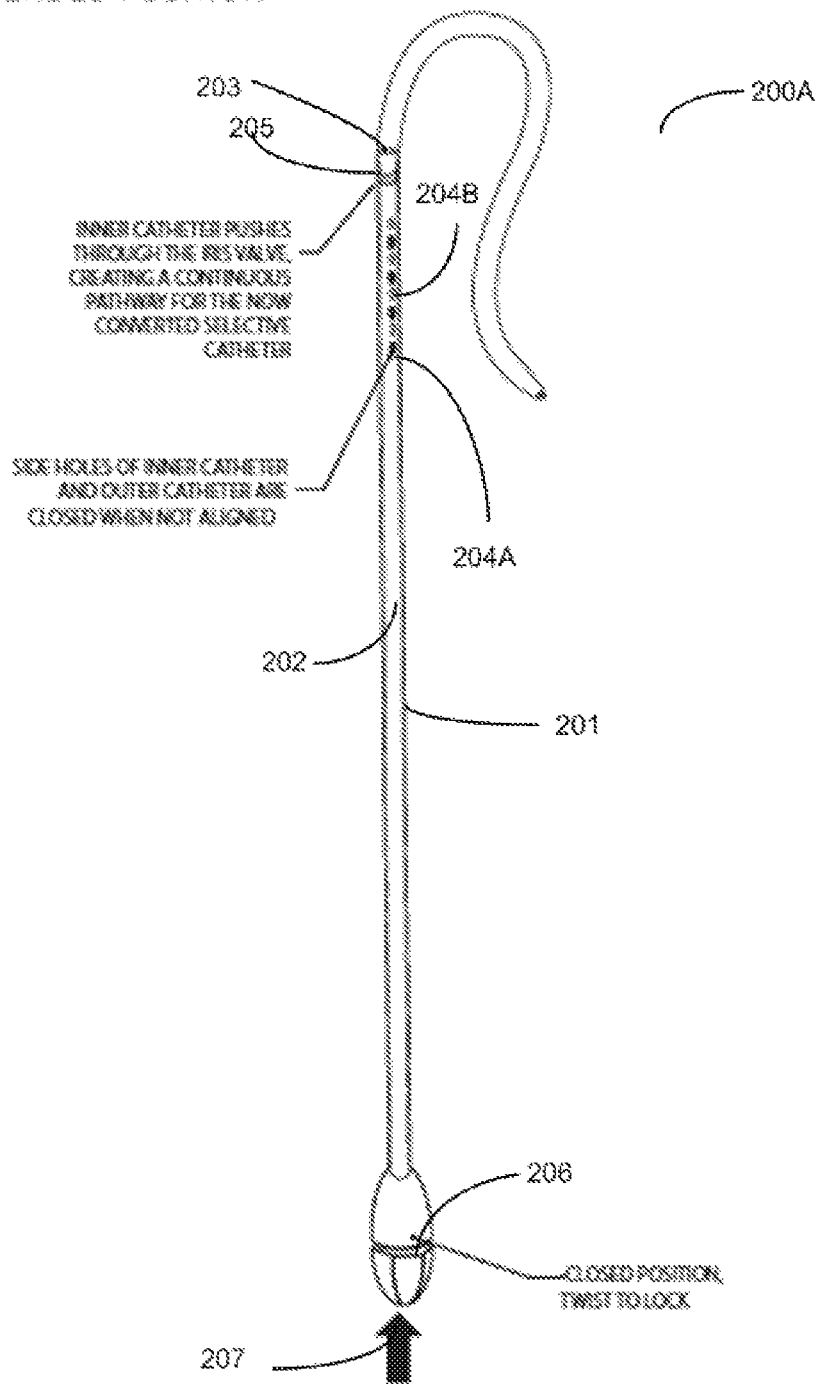
FIG. 2A is a diagrammatic representation of the catheter of FIG. 2 with the flush holes in the closed position in accordance with one embodiment of the invention.

FIG. 2 is a different embodiment of the flush/selective catheter 200. The implementation shown in 200 has an inner catheter 202 connected to a pull knob 209 and an outer catheter 201 that is close fitting over the inner catheter 202 and is connected to a hold knob 206. Both catheters have holes 204A and 204B, vertically aligned. These holes line up to configure the flush/selective catheter 200 into flush mode by pulling down on the knob 207 as shown in FIG. 200. An iris 205 in the outer catheter 201 is closed when the flush/selective catheter 200 is in the flush catheter configuration. FIG. 2A is a representation 200A of the flush/selective catheter 200 with the holes 204A and 204B missaligned for the flush/selective catheter 200 to be configured as a end hole catheter 200 A. When the flush/selective catheter is in the end-hole catheter mode as shown in FIG. 2A the end of the inner catheter 202 pushes through the iris 205 to open the inner catheter end 203 into the outer catheter 201.

Figure 3:
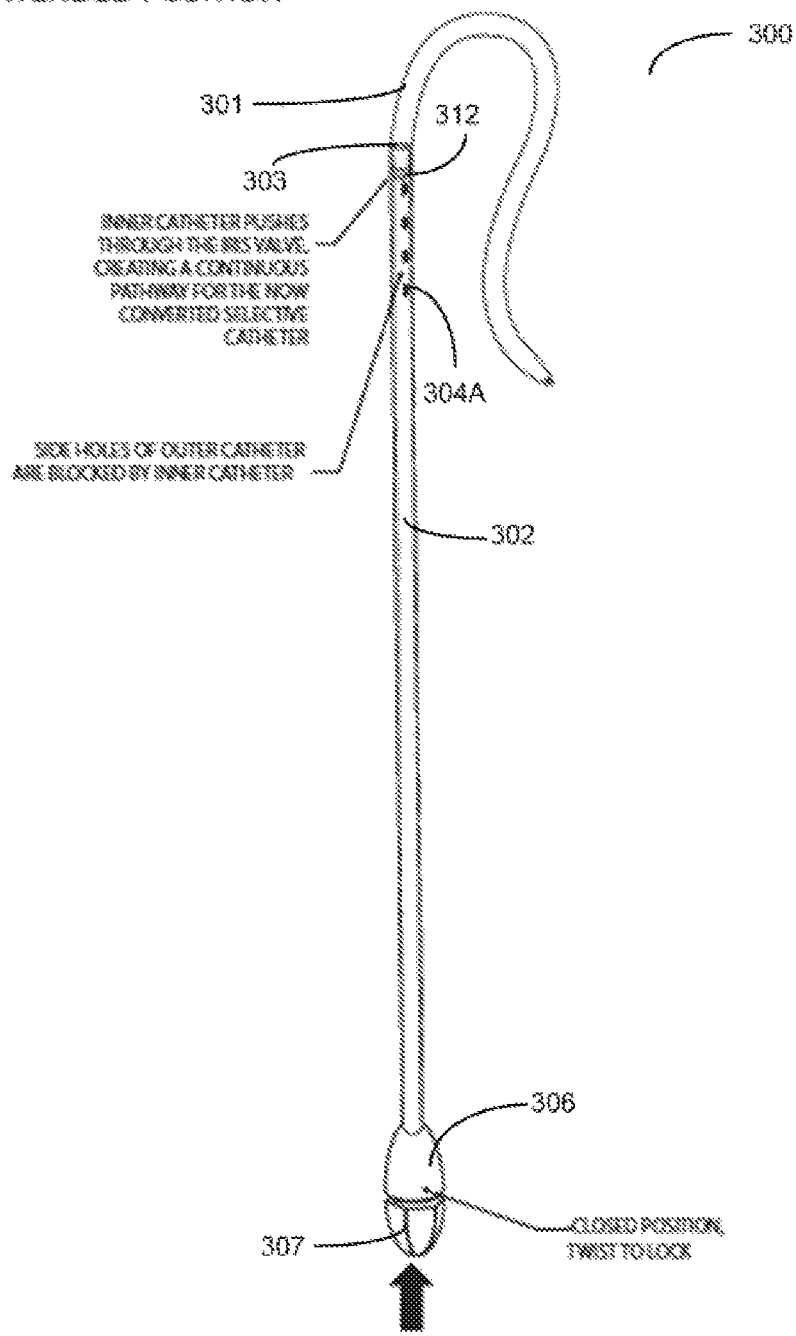
FIG. 3 is an exemplary diagrammatic representation of an interchangeable flush/selective catheter with the flush holes in a closed position in accordance with one embodiment of the invention.
Figure 3A:
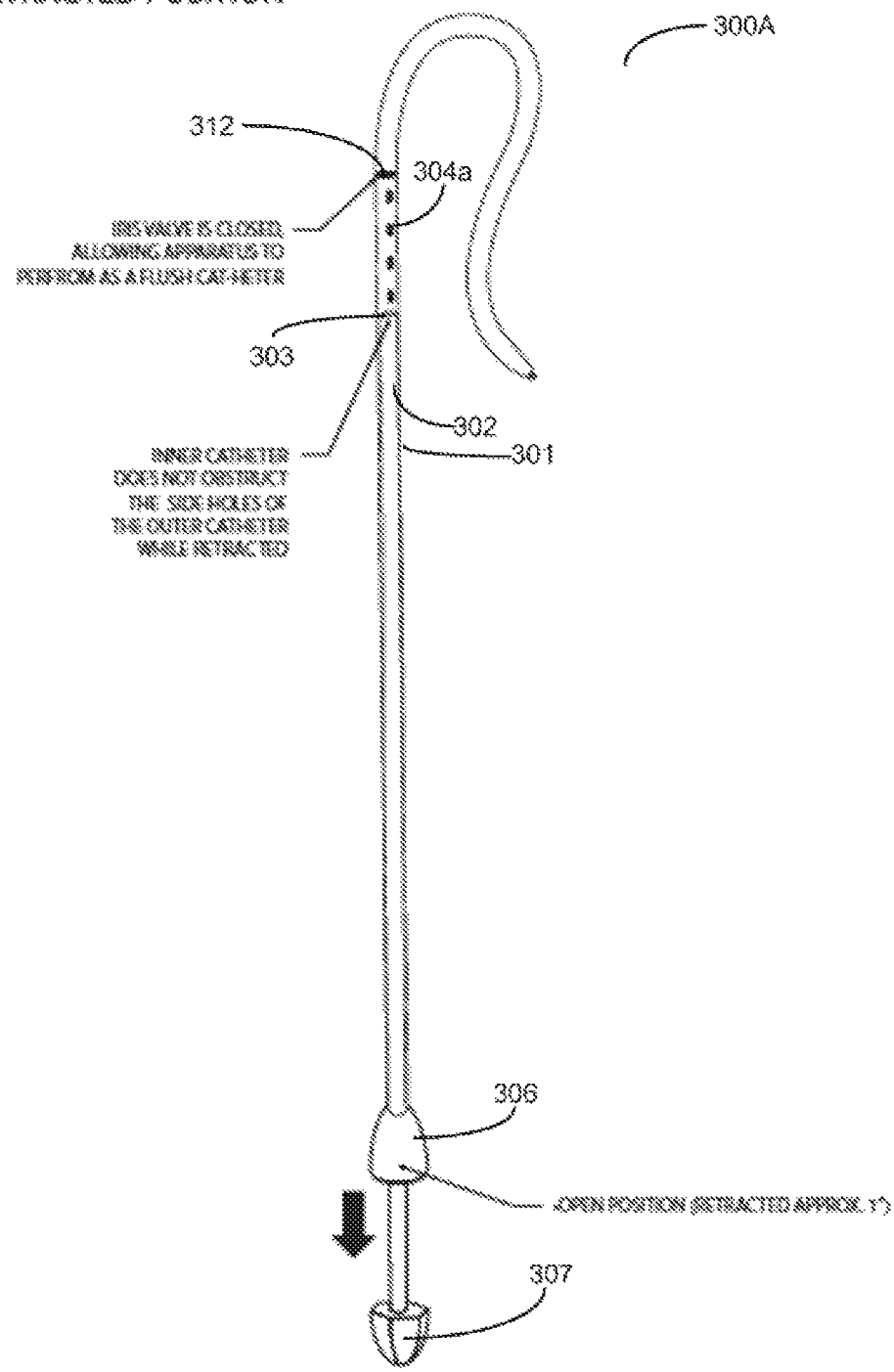
FIG. 3A is a diagrammatic representation of the catheter of FIG. 3 with the flush holes in an open position in accordance with one embodiment of the invention.

FIG. 3 is a third embodiment 300 of the flush/selective catheter. FIG. 3 shows the flush/selective catheter having an inner catheter 202 without any holes inside an outer catheter 301. The outer catheter 301 has holes 304A close to its distal end for providing the flush capability. The outer catheter is connected to a hold knob 306 and the inner catheter is connected to a pull knob 307. There is an iris 312 at a region within the outer catheter 30 that is closer to the distal end of the catheter than the holes 304A. When the flush/selective catheter is in the end hole catheter configuration, the pull knob 307 is flush with the hold knob 306 which pushes the inner catheter 302 up through the iris 312 and opens up the end 303 of the inner catheter 302 into the outer catheter 301. Since the inner catheter 302 has no holes the inner catheter blocks off the holes 304A of the outer catheter 301 preventing any flush action. FIG. 3A shows the flush/selective catheter 300 in the flush configuration 300A. To put the flush/select catheter in this mode the pull knob 307 is pulled out so that the end of the inner catheter 302 is pulled through the iris 312 allowing the iris to close blocking the flush/selective catheter 300A from being an end hole catheter. Further the inner catheter end 303 is pulled down below the level of the holes 304A in the outer catheter 301, to open the holes 304A. This allows the configured flush/selective catheter 300A to act as a flush catheter.

As will be understood by those familiar with the art, the invention may be embodied in other specific forms without departing from the spirit or essential characteristics thereof. Likewise, the particular naming and division of the members, features, attributes, and other aspects are not mandatory or significant, and the mechanisms that implement the invention or its features may have different structural construct, names, and divisions. Accordingly, the disclosure of the invention is intended to be illustrative, but not limiting, of the scope of the invention.

While the invention has been described in terms of several embodiments, those of ordinary skill in the art will recognize that the invention is not limited to the embodiments described, but can be practiced with modification and alteration within the spirit and scope of the appended claims. The description is thus to be regarded as illustrative instead of limiting. There are numerous other variations to different aspects of the invention described above, which in the interest of conciseness have not been provided in detail. Accordingly, other embodiments are within the scope of the claims.

The invention has been described in relation to particular examples, which are intended in all respects to be illustrative rather than restrictive. Those skilled in the art will appreciate that many different combinations will be suitable for practicing the present invention. Other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with a true scope and spirit of the invention being indicated by the following claims.

What is claimed is:

1. A convertible catheter configured with a dual functionality of a flush catheter and a selective catheter, the convertible catheter comprising:
    an outer catheter comprising at least one side, wherein the at least one side comprises at least one flush hole;
    an inner catheter inside the outer catheter, wherein the inner catheter is moveable within the outer catheter;
    the inner catheter comprising at least one side and a distal tip, wherein the at least one side comprises at least one flush hole and the distal tip comprises an opening;
    an occluding tip configured to selectively close or open the opening at the distal tip of the inner catheter; and
    an adapter configured to:
        move the inner catheter relative to the outer catheter to align the at least one flush hole on the at least one side of the inner catheter with the at least one flush hole on the at least one side of the outer catheter, and close the opening at the distal tip of the inner catheter via the occluding tip to convert the convertible catheter to the flush catheter to identify a process vessel, and
        move the inner catheter relative to the outer catheter to misalign the at least one flush hole on the at least one side of the inner catheter with at the at least one flush hole on the at least one side of the outer catheter, and open the opening at the distal tip of inner catheter via the occluding tip to convert the convertible catheter to the selective catheter to access a site of a procedure as a reverse curve catheter or a guide catheter.

2. The convertible catheter of claim 1, further comprising an occluding tip wire removably positioned in the inner catheter.

3. The convertible catheter of claim 2, wherein the occluding tip wire comprises the occluding tip configured to close and open the opening at the distal tip of the inner catheter.

4. The convertible catheter of claim 1, wherein the at least one flush hole on the at least one side of the inner catheter is aligned with the at least one flush hole on the at least one side of the outer catheter to create an open flush catheter hole.

5. The convertible catheter of claim 4, wherein the convertible catheter is configured as the flush catheter when the at least one flush hole is aligned with the at least one flush hole on the at least one side of the inner catheter.

6. The convertible catheter of claim 1, wherein the adapter comprises a Tuchy-Borst adapter.

7. The convertible catheter of claim 1, wherein the adapter comprises a first connector connected to the inner catheter and a second connector attached to the outer catheter.

8. The convertible catheter of claim 7, wherein one of the connectors is configured to rotate relative to the other connector, to align and open the at least one hole of the outer catheter to convert the convertible catheter to the flush catheter, and to misalign and close the at least one hole of the inner catheter to convert the convertible catheter to the selective catheter.

9. The convertible catheter of claim 1, wherein the adapter comprises a pull knob connected to the selective catheter and a hold knob connected to the flush catheter, and wherein the pull knob is configured to pull the flush catheter relative to the selective catheter to misalign at least one flush hole on the at least one side of the inner catheter with the at least one flush hole on the at least one side of the outer catheter.

* * * * *